United States Patent [19]
Nuss et al.

[11] Patent Number: 6,024,759
[45] Date of Patent: Feb. 15, 2000

[54] METHOD AND APPARATUS FOR PERFORMING PECTUS EXCAVATUM REPAIR

[75] Inventors: Donald Nuss, Norfolk, Va.; Francois Beuse, Callahan; Kevin T. Stone, Jacksonville, both of Fla.; Daniel Croitoru, Norfolk, Va.; Jeffrey David Gordon, Orange Park, Fla.; Jeffrey A. Duncan; Brian S. Schumacher, both of Jacksonville, Fla.

[73] Assignee: Walter Lorenz Surgical, Inc., Jacksonville, Fla.

[21] Appl. No.: 09/074,969

[22] Filed: May 8, 1998

[51] Int. Cl.$^7$ .................................................. A61F 5/01
[52] U.S. Cl. ............................................ 606/237; 606/60
[58] Field of Search .................................... 600/204, 210, 600/235; 606/237, 238, 60

[56] References Cited

U.S. PATENT DOCUMENTS

| | | |
|---|---|---|
| 2,695,607 | 11/1954 | Hipps et al. . |
| 3,946,728 | 3/1976 | Bettex . |
| 4,201,215 | 5/1980 | Crossett et al. . |
| 5,520,609 | 5/1996 | Moll et al. .............................. 600/204 |

OTHER PUBLICATIONS

American v. Mueller, Sternum Instruments, p. 345 (1 sheet).
Current Problems in Surgery, Congenital Chest Wall Deformities, vol. XXXIII, No. 6, 1996, pp. 470–543.

A. Lincoln Brown, M.D., Pectus Excavatum, Journal of Thoracic Surgery, pp. 164–184.

Alton Ochsner, M.D. and Michael DeBakey, M.D., The Journal of Thoracic Surgery, vol. 8, No. 5, Jun., 1939, pp. 469–511.

Donald Nuss, Robert E. Kelly Jr, Daniel P. Croitoru, and Michael E. Katz, Journal of Pediatric Surgery, "A 10–Year Review of a Minimally Invasive Technique for the Correction of Pectus Excavatum", copyright 1998 by W.B. Saunders Company, pp. 545–552.

*Primary Examiner*—Michael H. Thaler
*Attorney, Agent, or Firm*—Harness, Dickey & Pierce, P.L.C.

[57] ABSTRACT

A method and apparatus for performing pectus excavatum repair on a deformed sternum. The apparatus includes an elongated pectus bar having a first end and a second end. The elongated pectus bar provides a minimum bendable strength of about 65 in-lbs or a minimum material yield strength of $35 \times 10^6$ psi or a minimum bendable stiffness of about 1000 lb-in$^2$. The elongated pectus bar is shaped into a convexly curved pectus bar. The convexly curved bar is passed under the deformed sternum with the convexity facing posteriorly. The elongated pectus bar is then rotated so that the convexity faces anteriorly such that the deformed sternum is raised into a desired position.

33 Claims, 6 Drawing Sheets

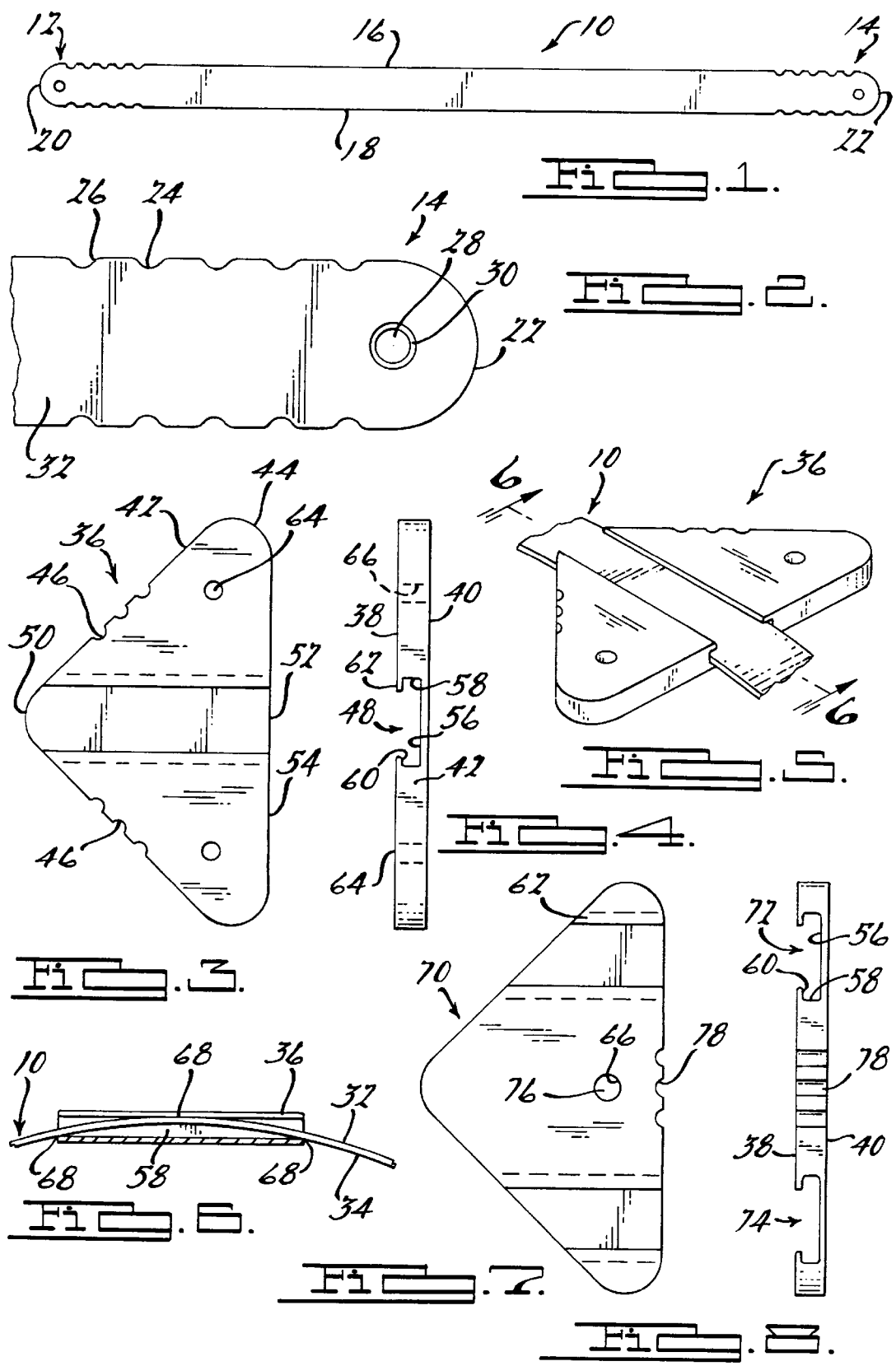

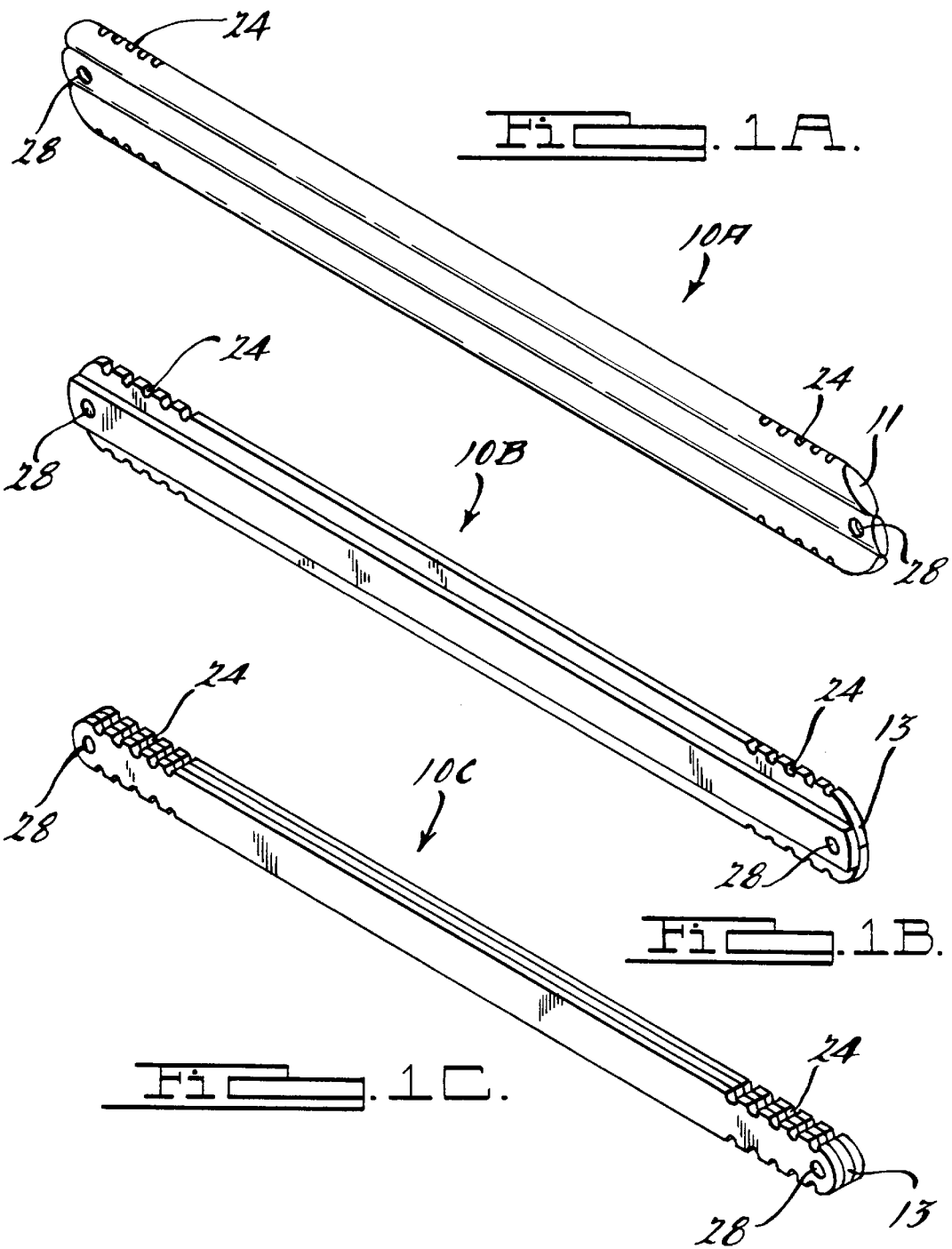

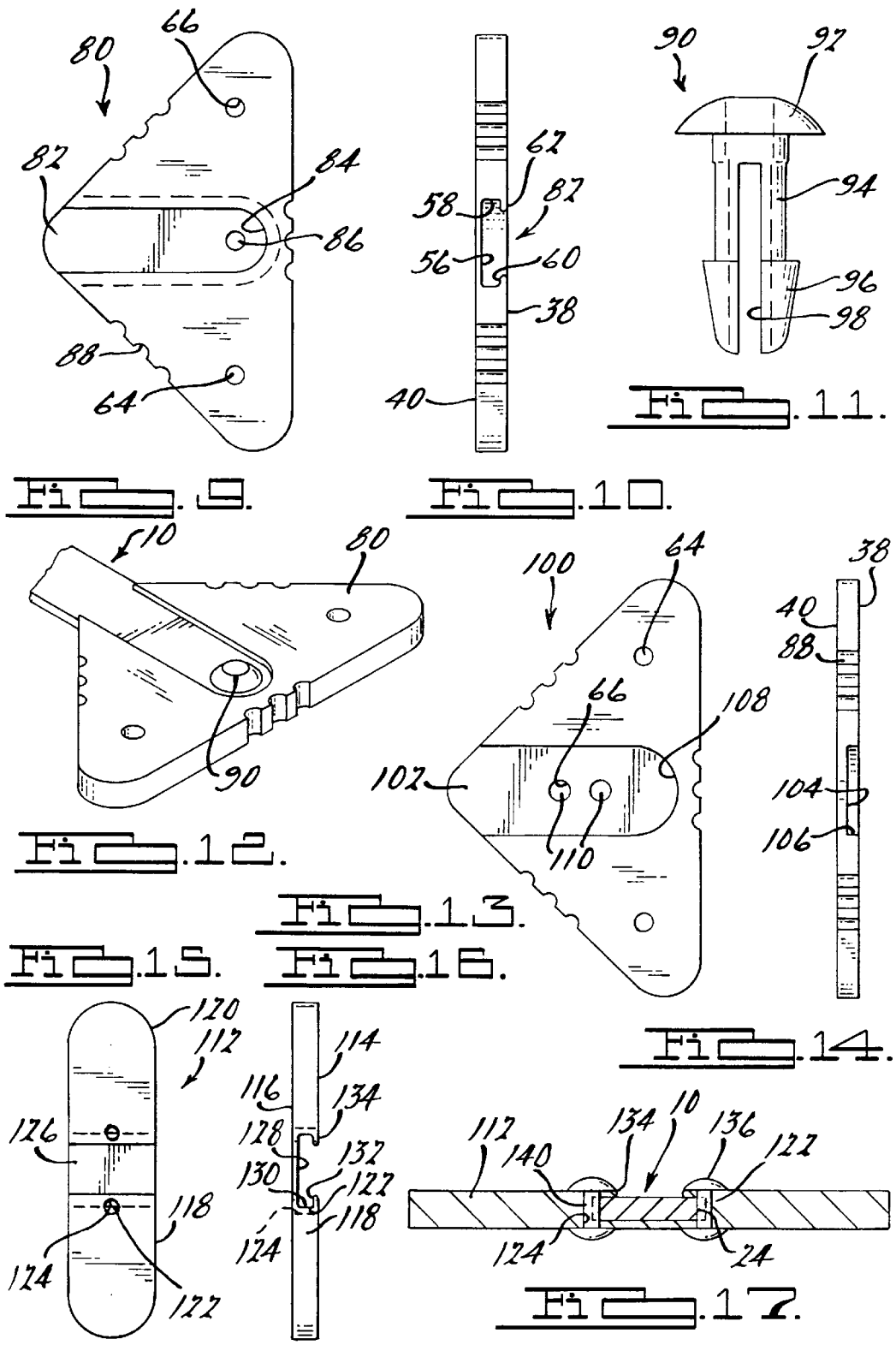

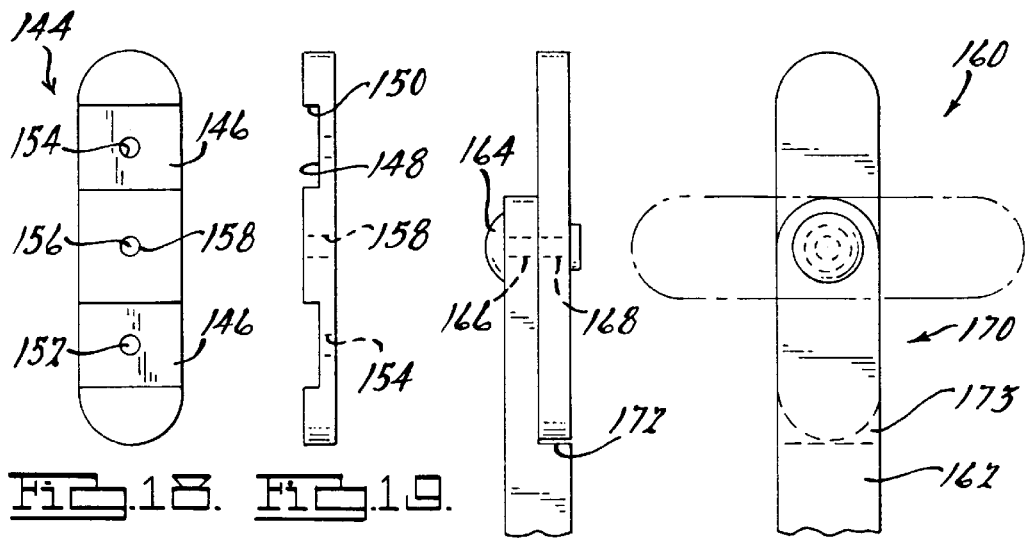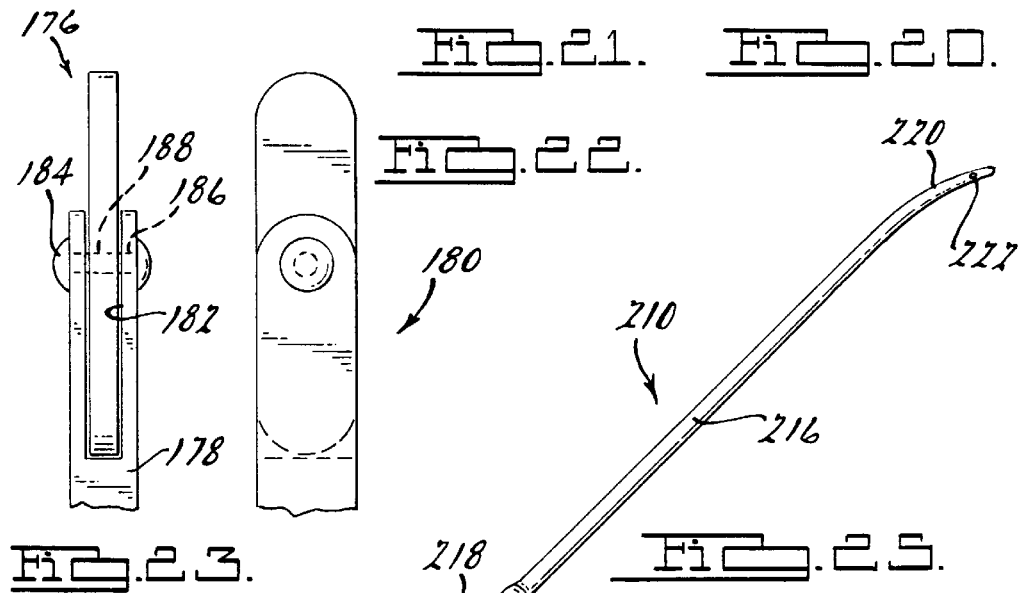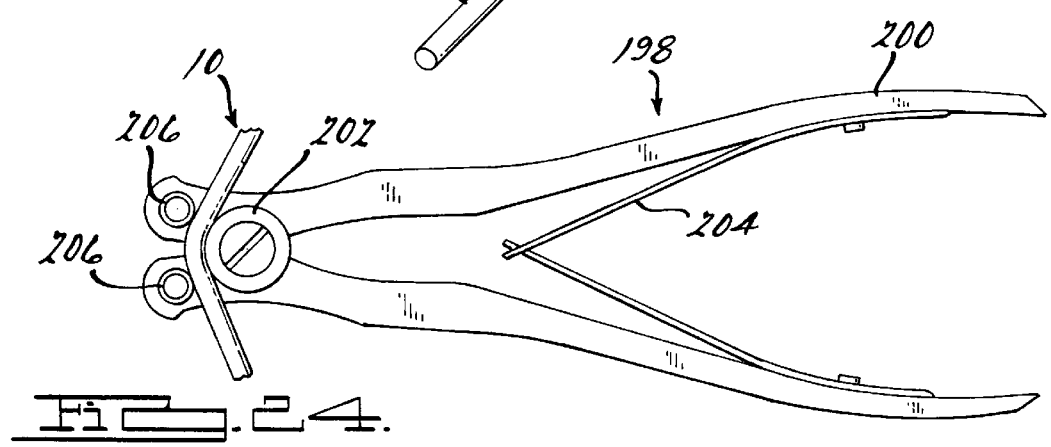

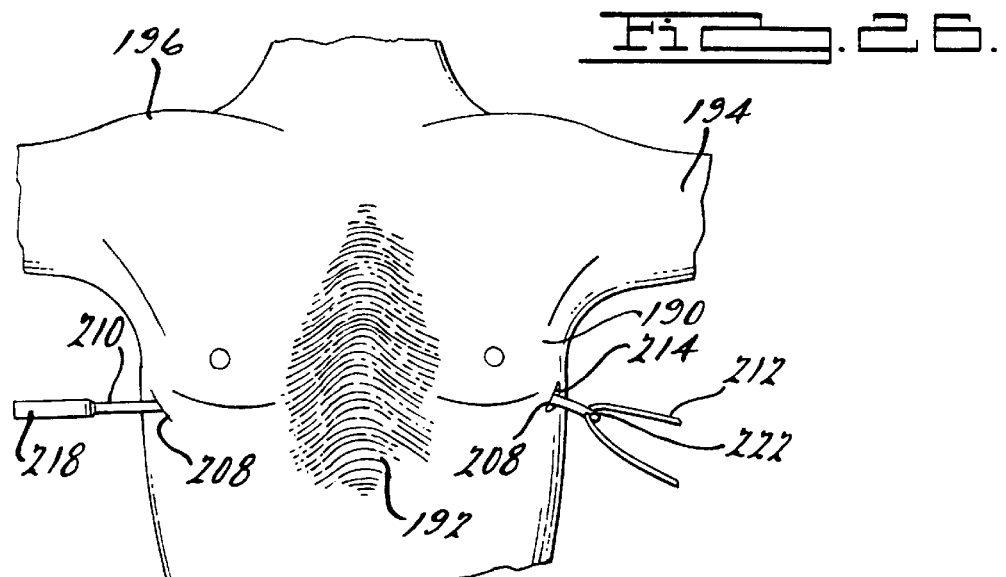
Fig. 26.
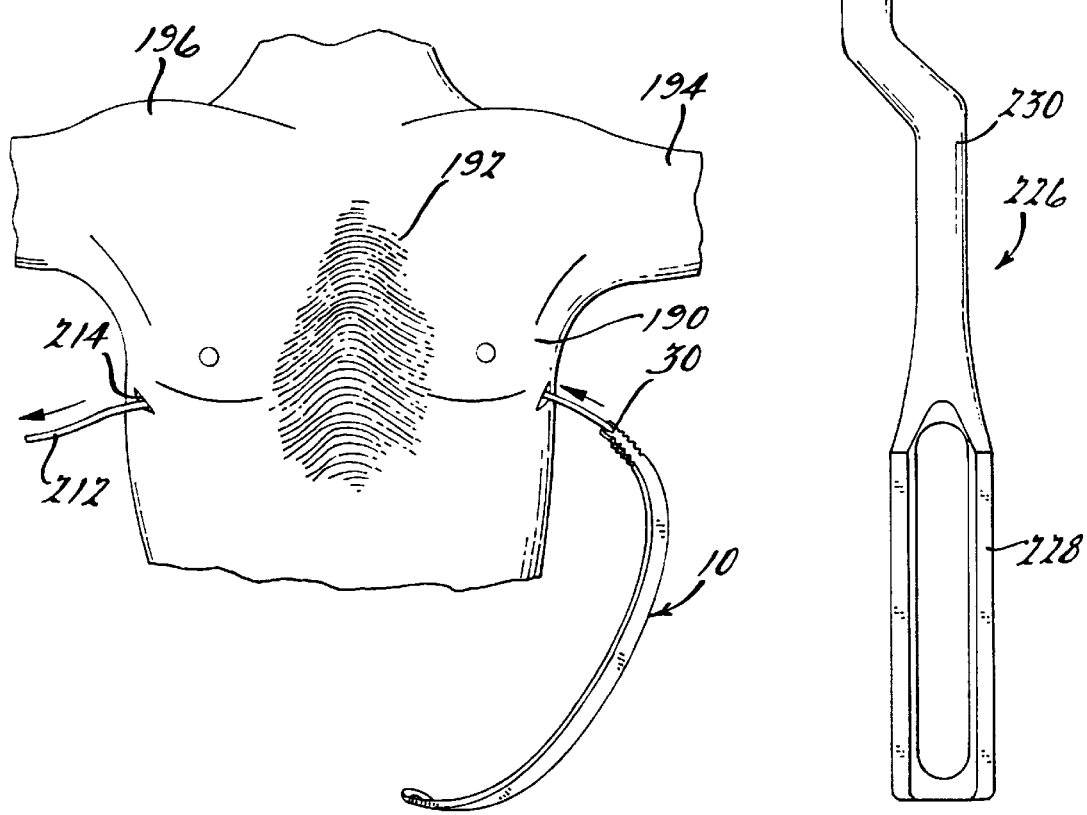
Fig. 27.
Fig. 28.

METHOD AND APPARATUS FOR PERFORMING PECTUS EXCAVATUM REPAIR

BACKGROUND OF THE INVENTION

1. Field of the Invention

This invention relates generally to a method and apparatus for use in surgical procedures, and more particularly, to a method and apparatus for performing pectus excavatum repair.

2. Discussion of the Related Art

Pectus excavatum, also known as funnel chest, is one of the most common anterior chest wall deformities. Patients exhibiting this deformity range from having a mildly depressed sternum to other extreme cases in which the sternum is positioned substantially adjacent to the vertebrae column. This depression or deformity is produced by posterior depression of the sternum and the lower costal cartilages. Specifically, the body of the sternum is generally angled posteriorly towards the vertebrae generally starting below the second costal cartilage. The costal cartilages are then angled posteriorly to meet the sternum, thereby creating a depression in the chest wall.

Surgical repair of pectus excavatum dates back for many years. A history of such surgical repairs is set forth in an article entitled "Congenital Chest Wall Deformities" which is set forth in "Current Problems In Surgery", Volume XXXIII, No. 6, June 1996, which is hereby incorporated by reference. In general, the current surgical repair techniques all involve resection of the deformed costal cartilage and sternal osteotomy. In this regard, the sternum is separated and elevated anteriorly and supported by securing the sternum with a variety of internal fixation devices.

One of these devices is produced by V. Mueller and is known as an Adkins Strut. This strut generally consists of an elongated rectangular shaped bar having a rectangular cross-section that can be bent manually to hold the sternum in a slightly over-corrected position. This strut is generally laid behind the lower half of the body of the sternum, with the separated sternum laid atop the strut. The strut is anchored on each side at the appropriate position to a rib exposed by a myotomy through the pectoral muscles. Holes positioned at each end of the strut are then used to facilitate fixation by means of sutures. This strut has a thickness of 1.5 mm, provides an estimated bendable strength of about 24 in-lbs (inch-pounds) and a bendable stiffness of about 232 lb-in$^2$ (pounds times inches squared), as estimated and determined in accordance with the procedure set forth in ASTM (American Standard Test Method) F382 and further discussed herein. This strut also has an estimated yield strength of about 25×10$^6$ psi (pounds per square inch) based upon the material used for this strut.

However, use of the above-identified procedures and internal fixation devices suffer from many disadvantages. For example, in each of the noted surgical procedures, resection of the costal cartilage and sternal osteotomy is performed which is a long and complex surgical procedure that has considerable blood loss and a significant complication rate. Moreover, such surgery produces an unsightly scar in the anterior chest area. It has also been found that the use of the internal fixation strut produced by V. Mueller has a bendable strength, bendable stiffness and yield strength which are not sufficient to support the sternum in Applicants' new minimally invasive technique. This strut further does not provide for stabilization of the strut ends by means other than fixation with sutures which is generally not sufficient in many adolescent patients and older or for Applicants' new procedure. Furthermore, the blunt or squared ends of this bar are also difficult to guide through a patient and may tear and catch on soft tissue.

What is needed then is a method and apparatus for performing pectus excavatum repair which does not suffer from the above mentioned disadvantages. This in turn, will provide a minimally invasive technique which does not require cartilage resection or sternal osteotomy, eliminates the need to raise pectoralis muscle flaps, reduces surgical complexity, reduces blood loss, reduces surgical time and cost, eliminates any anterior chest wall incision or scar, provides early return to full activities, provides normal long term chest strength, expansion, flexibility and elasticity, and provides excellent long term cosmetic results. It is, therefore, an object of the present invention to provide such a method and apparatus for performing pectus excavatum repair.

SUMMARY OF THE INVENTION

In accordance with the teachings of the present invention, a method and apparatus for performing pectus excavatum repair on a deformed sternum is disclosed. This is basically achieved by providing an elongated bar having minimum bendable strength, a minimum bendable stiffness, or a minimum yield strength. The bar is preferably bent in a convex manner and inserted with the convexity facing posteriorly and thereafter rotated with the convexity facing anteriorly.

In one preferred embodiment, an apparatus for performing pectus excavatum repair on a deformed sternum includes an elongated pectus bar. The elongated pectus bar has a first end and a second end with a minimum bendable strength of about 65 in-lbs. The elongated pectus bar is operable to retrain the deformed sternum into a desired shape.

In another preferred embodiment, an apparatus for performing pectus excavatum repair on a deformed sternum also includes an elongated pectus bar. The elongated pectus bar has a first end and a second end with a minimum bendable stiffness of about 1000 lb-in$^2$. The elongated pectus bar is operable to retrain a deformed sternum into a desired shape.

In yet another preferred embodiment, an apparatus for performing pectus excavatum repair on a deformed sternum also includes an elongated pectus bar. The elongated pectus bar has a first end and a second end with a yield strength of at least about 35× 10$^6$ psi. The elongated bar is operable to retrain the deformed sternum into a desired shape.

In another preferred embodiment, a method for performing pectus excavatum repair on a deformed sternum includes the steps of providing an elongated pectus bar having a first end and a second end, shaping the pectus bar into a convexly curved pectus bar, passing the pectus bar under the deformed sternum with the convexity facing posteriorly, and rotating the pectus bar so that the convexity faces anteriorly, whereby the deformed sternum is raised into a desired position.

BRIEF DESCRIPTION OF THE DRAWINGS

Still other advantages of the present invention will become apparent to those skilled in the art after reading the following specification and by reference to the drawings in which:

FIG. 1 is a top elevational view of a pectus bar for performing pectus excavatum repair according to the teachings of a first preferred embodiment of the present invention;

FIG. 1A is a perspective view of a pectus bar for performing pectus excavatum repair according to the teachings of a second preferred embodiment of the present invention;

FIG. 1B is a perspective view of a pectus bar for performing pectus excavatum repair according to the teachings of a third preferred embodiment of the present invention;

FIG. 1C is a perspective view of a pectus bar for performing pectus excavatum repair according to the teachings of a fourth preferred embodiment of the present invention;

FIG. 2 is an enlarged top elevational view of the pectus bar of FIG. 1;

FIG. 3 is a top elevational view of a stabilizer for performing pectus excavatum repair according to the teachings of a first preferred embodiment of the present invention;

FIG. 4 is a right side elevational view of the stabilizer of FIG. 3;

FIG. 5 is a perspective view of the pectus bar of FIG. 1 assembled with the stabilizer of FIG. 3;

FIG. 6 is a side cross-sectional view of the assembly of FIG. 5 taken along line 6—6 of FIG. 5;

FIG. 7 is a top elevational view of a stabilizer for performing pectus excavatum repair according to the teachings of a second preferred embodiment of the present invention;

FIG. 8 is a right side elevational view of the stabilizer of FIG. 7;

FIG. 9 is a top elevational view of a stabilizer for performing pectus excavatum repair according to the teachings of a third preferred embodiment of the present invention;

FIG. 10 is a left side elevational view of the stabilizer of FIG. 9;

FIG. 11 is a side elevational view of a rivet for performing pectus excavatum repair according to the teachings of the present invention;

FIG. 12 is a perspective view of the pectus bar of FIG. 1 assembled with the stabilizer of FIG. 9 and the rivet of FIG. 11;

FIG. 13 is a top elevational view of a stabilizer for performing pectus excavatum repair according to the teachings of a fourth preferred embodiment of the present invention;

FIG. 14 is a left side elevational view of the stabilizer of FIG. 13;

FIG. 15 is a top elevational view of a stabilizer for performing pectus excavatum repair according to the teachings of a fifth preferred embodiment of the present invention;

FIG. 16 is a left side elevational view of the stabilizer of FIG. 15;

FIG. 17 is an assembled side cross-sectional view of the stabilizer of FIG. 15 utilizing a pair of bolts to secure the stabilizer of FIG. 15 to the pectus bar of FIG. 1;

FIG. 18 is a top elevational view of a stabilizer for performing pectus excavatum repair according to the teachings of a sixth preferred embodiment of the present invention;

FIG. 19 is a right side elevational view of the stabilizer of FIG. 18;

FIG. 20 is a top elevational view of a stabilizer for performing pectus excavatum repair according to the teachings of a seventh preferred embodiment of the present invention;

FIG. 21 is a left side elevational view of the stabilizer of FIG. 20;

FIG. 22 is a top elevational view of a stabilizer for performing pectus excavatum repair according to the teachings of a eighth preferred embodiment of the present invention;

FIG. 23 is a right side elevational view of the stabilizer of FIG. 22; and

FIGS. 24–32 illustrate a method for performing pectus excavatum repair applying the pectus bar of FIG. 1, the stabilizer of FIG. 3 along with instrumentation used during the surgical procedure.

DETAILED DESCRIPTION OF THE PREFERRED EMBODIMENT(S)

Figure 29:
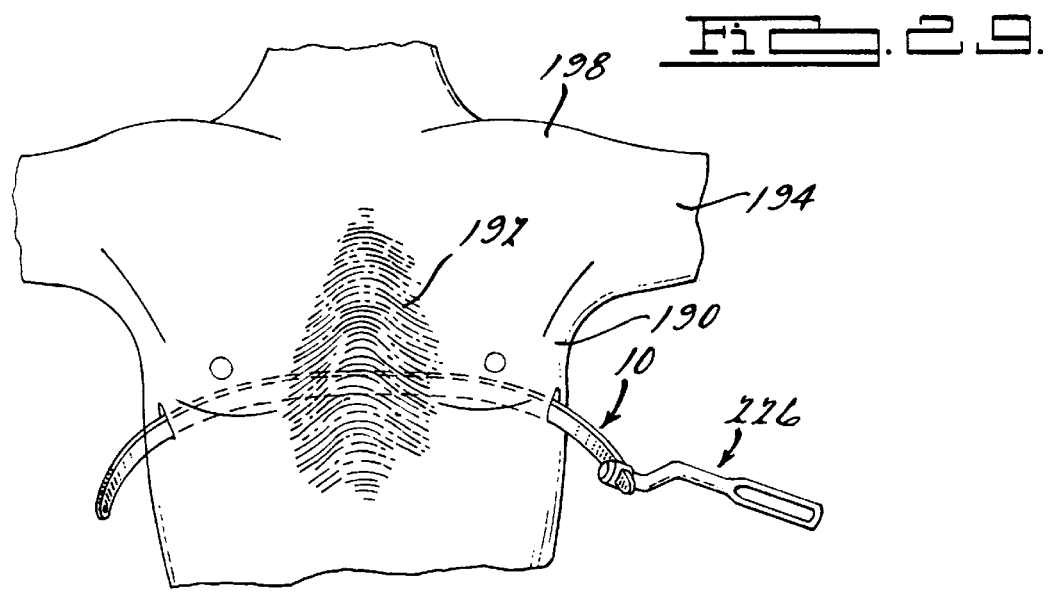

The following description of the preferred embodiments concerning a method and apparatus for performing pectus excavatum repair during surgical procedures are merely exemplary in nature and are not intended to limit the invention or its application or uses. Moreover, it is to be understood that the term pectus bar as used herein may refer to a single pectus bar or multiple bars positioned or aligned adjacent one another to form the pectus bar with either the single pectus bar or the multiple bars combined providing at least the minimum bendable strength, bendable stiffness or yield strength, as further described herein.

Referring to FIGS. 1–2, a pectus bar 10 according to the teachings of a first preferred embodiment of the present invention is shown. The pectus bar 10 is an elongated bar having a lateral rectangular cross-section with a first end 12 and a second end 14. The pectus bar 10 is provided in various sizes having a length between about 7 inches to about 15 inches with each size varying by about 1 inch. The thickness of the pectus bar 10 preferably ranges between about 1.5 mm to about 4.5 mm and the width preferably varies between about 5 mm to about 20 mm. However, should there be additional clearance, the pectus bar 10 may be thicker or wider. The pectus bar 10 includes a pair of opposing planar sidewalls 16 and 18 and a pair of opposing arcuate sidewalls 20 and 22.

Referring to FIG. 2, the second end 14 of the pectus bar 10 is shown in an enlarged view with the understanding that the first end 12 is a mirror image of the second end 14. The second end 14 includes the arcuate sidewall 22 which is generally a half circle. Each sidewall 16 and 18 define a plurality of arcuate notches or scallops 24 having arcuate corners 26 to eliminate any sharp contours. Each sidewall 16 and 18 includes five (5) notches 24, however, those skilled in the art would recognize that fewer or more notches may also be provided. The notches 24 are essentially used for securing the pectus bar 10 by wrapping sutures about the notches 24. A hole 28 having a chamfer 30 is defined by the pectus bar 10 and is perpendicular to a first planar surface 32 and opposing planar surface 34 (see FIG. 6). The hole 28 may further be used for securing the pectus bar 10, via sutures passing therethrough or for securing the pectus bar 10 to a stabilizer, further discussed herein.

The pectus bar 10 is provided in a straight or flattened condition which is subsequently shaped to match a desired chest contour during surgery. As previously indicated, the pectus bar 10 has a thickness between the range of about 1.5 mm to about 4.5 mm. The width of the pectus bar 10 is between the range of about 5 mm to about 20 mm. In this regard, the cross-sectional area ranges between about 7.5 $mm^2$ to about 90 $mm^2$ with the thicker bars or larger cross-sectional area exhibiting a higher bending stiffness and bending strength.

Specifically, the minimum required bending strength and the minimum required bending stiffness needed to train and shape the sternum should be about 65 in-lbs and 1000 lb-in$^2$, respectively, as defined using ASTM Method F382-95. In addition, the material selected should have a minimum yield strength of about $35 \times 10^6$ psi. It should be noted that the minimum bending strength, bending stiffness, and yield strength are far in excess of that determined to be exhibited by the prior art Mueller bar. For example, upon testing six pectus bars 10, each having a thickness of 2.8 mm and a length of 13 inches with each made from cold-worked 316 LVM stainless steel, an average bending strength of 174 in-lbs and an average bending stiffness of 1283 lb-in$^2$ was determined. Moreover, based upon the material selected, these pectus bars exhibit a yield strength of about $135 \times 10^6$ psi. The bending strengths and bending stiffnesses are based upon ASTM F382 test method set forth below which identifies the test materials, equipment, procedure and results.

Materials & Equipment
1. Sternum Plate: Six (6) plates with a length of 13" and all plates made from 316 LVM stainless steel and each are 2.8 mm thick.
2. Test Fixture: Four point bend fixture with ⅜" diameter rollers at loading and support locations. The distance h and k, as defined in ASTM F382-95, were 1.5".
3. Test Machine: Servo-hydraulic test machine from Interlaken Technology Corp. (Eden Prairie, Minn.). Machine was operated in displacement control at a rate of 0.50"/min. Load and displacement data was recorded at a sampling rate of 4 points/sec.

Procedure
1. The test was conducted in accordance with ASTM Method F382-95.
2. Load vs. displacement curves were plotted for each plate. The slope and proof load values, as defined in ASTM F382-95, were calculated from the curves.

Results

Table 1 summarizes the results from the test. The average bending strength is 174 in-lbs. The average bending stiffness for the plates is 1283 lb-in$^2$, as defined in ASTM F382-95.

TABLE 1

Results

| Specimen # | Load, P (lbs) | Slope, S (lb/in) | Equiv. Bending Stiffness, E (lb-in$^2$) | Bending Strength (in-lb) |
| --- | --- | --- | --- | --- |
| Specimen 1 | 235 | 928 | 1305.0 | 176.3 |
| Specimen 2 | 228 | 904 | 1271.3 | 171.0 |
| Specimen 3 | 236 | 925 | 1300.8 | 177.0 |
| Specimen 4 | 238 | 940 | 1321.9 | 178.5 |
| Specimen 5 | 219 | 880 | 1237.5 | 164.3 |
| Specimen 6 | 232 | 896 | 1260.0 | 174.0 |
| Average | 231 | 912 | 1283 | 174 |

The pectus bar is preferably made from cold-worked 316 LVM stainless steel to deliver the above desired bending strength and bending stiffness within the desired thickness and cross-sectional area ranges which are above the minimum bending strength and stiffness required. Moreover, the material selected for the pectus bar also provides a yield strength of $135 \times 10^6$ psi which is also above the minimum yield strength needed to reach a successful result. Those skilled in the art will also recognize that various other bio-compatible materials can also be utilized such as titanium, cobalt-chrome, etc. Moreover, various resorbable material that can be shaped may also be used for the pectus bar 10 as long as it provides the above-identified minimum bending strength, stiffness of the bar or yield strength within the desired thickness and cross-sectional area ranges. These resorbable materials include, but are not limited to, any of a family of resorbable materials including polymers and copolymers of PLLA, PGA, PDLA, etc. or any of the resorbable materials set forth in U.S. Pat. No. 5,569,250 which is hereby incorporated by reference.

In addition, it should further be noted that each of the characteristics of bending strength, bending stiffness and yield strength are independent from one another. Therefore, by providing a single pectus bar 10, which may include a plurality of adjacent bars, that meets any one of the minimum bending strength, bending stiffness or yield strength requirement from a single bar or accumulative from the multiple bars will enable successful treatment of this deformity. The increase in the bending strength, bending stiffness and yield strength is also required to achieve the successful result, since the shape of the sternum is actually retrained to maintain a new desired shape without a sterno-osteotomy or cartilage resection as previously performed in the prior art using the prior art strut from the V. Mueller, as noted above. Finally, it should further be noted that it is preferred that the minimum bending strength or bending stiffness be exhibited throughout the length of the pectus bar. However, in some instances these minimum requirements may be exhibited along only a portion of the pectus bar 10.

Turning now to FIGS. 1A–1C, pectus bars 10A–10C are shown in alternate preferred embodiments. In this regard, pectus bar 10A includes three (3) independent elongated cylindrical bars 11 which are positioned substantially adjacent to one another. The cylindrical bars 11 may be linked together by any appropriate means, such as metal bands, welding, etc. or may merely be located adjacent one another independently. The pectus bar 10B is shown including three (3) staggered elongated rectangular shaped bars 13 also aligned and positioned adjacent one another to form the single pectus bar 10B. The pectus bar 10C also includes the three (3) elongated rectangular bars 13 stacked atop one another, as shown clearly in FIG. 1C. Each of the pectus bars 10A, 10B and 10C are employed substantially similar to the pectus bar 10 further described herein. In this regard, pectus bars 10A, 10B and 10C may be affixed to the various embodiments of the stabilizers disclosed herein, may include arcuate or rounded ends, as well as include notches or bores for assisting in securing the pectus bars 10A, 10B and 10C within the patient, as described with respect to pectus bar 10. It should also be understood that the pectus bars 10A, 10B and 10C may be formed from more or less than the three (3) bars shown.

Turning now to FIGS. 3–4, an isosceles triangular shaped stabilizer 36 according to the teachings of a first preferred embodiment of the present invention is shown. The stabilizer 36 is designed to be received on one or both ends 12 and 14 of the pectus bar 10 in order to stabilize the positioning and placement of the pectus bar 10 within a patient, further discussed herein. The stabilizer 36 is also preferably constructed from cold-worked 316 LVM stainless steel or any other biocompatible material as set forth above, including any resorbable material, such as Lactosorb provided by Biomet, Inc. of Warsaw, Ind.

The stabilizer 36 has a first planar surface 38, a second planar surface 40 and is defined by a substantially triangular shaped sidewall 42 having rounded corners 44. The sidewall 42 defines two sets of three notches 46, each again used for retaining the stabilizer 36, via sutures wrapped about the notches 46. A dove tail groove or channel 48 runs from a first rounded corner 50 to a center 52 of a side 54. The channel 48 is defined by a first planar sidewall 56, opposing perpendicular sidewalls 58 and inner sidewalls 60 of flange 62. The mating shape could be triangular or any shape that allows mating of the components. The slot or channel 48 is operable to slidably receive either end 12 or 14 of the pectus bar 10. The stabilizer plate 36 also defines a pair of holes or bores 64 defined by a sidewall 66.

Referring to FIGS. 5–6, the stabilizer 36 is shown slidably received within the pectus bar 10. In this regard, the second end 14 of the pectus bar 10 is shown having an arcuate shape to meet the contour of the chest cavity. The sidewalls 58 of the channel 48 provide for a clearance of the curved pectus bar 10, as shown in FIG. 6. This curvature of the pectus bar 10 is used to snuggly secure the pectus bar 10 relative to the stabilizer 36 along substantially three contact points 68. As was previously noted, the stabilizer 36 will generally be sutured on both the first end 12 and the second end 14 of the pectus bar 10 to ensure that the pectus bar 10 is fixedly retained within the chest cavity upon implantation.

Turning to FIGS. 7–8, a stabilizer 70 according to the teachings of a second preferred embodiment in the present invention, is shown. In this regard, like reference numerals will be used to identify like structures with respect to the first preferred stabilizer 36. The stabilizer 70 is substantially similar to the stabilizer 36, except for defining a first channel 72 and a second channel 74 along with defining a centrally positioned hole 76 and three notches 78 positioned adjacent thereto. Here again, the hole 76 is defined by the sidewall 66 and the notches 78 are used to receive sutures for securing the stabilizer 70 relative to the chest cavity. The first channel 72 and the second channel 74 allow for a pair of pectus bars 10 to be joined substantially parallel to one another to provide even further contouring and shaping capabilities which may be required for more severe deformities. The channels 72 and 74 are also operable to slidably receive pectus bars 10 and the contour of the pectus bars 10 are operable to snuggly secure the pectus bars 10 relative to the stabilizer 70.

Turning to FIGS. 9–12, a stabilizer 80 according to the teachings of a third preferred embodiment of the present invention, is shown. Here again, like reference numerals will be used to identify like structures with respect to the first preferred stabilizer 36. The stabilizer 80 is substantially similar to the stabilizer 36 except that the stabilizer 80 defines a channel 82 having a rounded closed end 84 with a hole 86 defined by sidewall 66 positioned adjacent thereto. In addition, each side of the triangular shaped sidewall 42 includes a set of three notches 88. The endwall 84 along with the hole 86 is substantially aligned with the hole 28 and each end 12 and 14 of the pectus bars 10.

A rivet 90 is operable to be passed through both holes 28 and 86 of the pectus bar 10 and stabilizer 80, respectively, to fixedly secure the stabilizer 80 relative to the pectus bar 10. The rivet 90, as shown in FIG. 11, includes an arcuate shaped head 92, a cylindrical shaft portion 94 and a conically shaped locking portion 96. Passing through the cylindrical shaft 94 and the conically shaped portion 96 is a U-shaped groove 98 which enables the rivet 90 to flex upon passing the rivet 90 through holes 28 and 86. Those skilled in the art would also recognize that various other coupling elements or mechanisms such as a nut and bolt, machine screw, etc. could also be used to secure the stabilizer 80 relative to the pectus bar 10. It should further be noted that the hole 86 and the stabilizer 80 may also be used in combination with the stabilizer 36 or 70 along their respective channels. Moreover, multiple holes along both the pectus bar 10 and the respective channels may also be used should it be desired to provide further securement. In this regard, FIG. 12 shows the stabilizer 80 secured to the second end 14 of the pectus bar 10 with the rivet 90.

Referring now to FIGS. 13–14, a stabilizer 100 according to the teachings of a fourth preferred embodiment in the present invention, is shown. In this regard, like reference numerals will be used to identify similar structures with respect to the other preferred stabilizers. The stabilizer 100 is substantially similar to the stabilizer 80 except that the stabilizer 100 includes a channel 102 defined by a first planar sidewall 104 and opposing perpendicular sidewalls 106 having a rounded end 108. The channel 102 does not include the upturned flange 62, which thereby provides further versatility with regard to attaching and aligning the stabilizer 100 relative to the pectus bar 10. The channel 102 further includes a pair of holes 110 defined by sidewalls 66 which are designed to mate with a pair of holes 28 passing through each end 12 and 14 of the pectus bar 10. The two holes 110 are designed to operably receive the rivets 90 or other appropriate coupling mechanisms. The two holes 110 provide further securement of the stabilizer 10 relative to the pectus bar 10 since there is generally no three point contact 68 used with the stabilizer 100. Moreover, since there are two pairs of holes 110 which should be aligned with a pair of holes 28 in the pectus bar 10, the pectus bar 10 is generally not contoured along this area and remains substantially planar for hole alignment.

Turning to FIGS. 15–16, a stabilizer 112 according to the teachings of a sixth preferred embodiment of the present invention is shown. The stabilizer 112 includes a first planar surface 114, a second planar surface 116 with a substantially rectangular shaped sidewall 118 having rounded ends 120. The stabilizer 112 includes a pair of holes 122 defined by sidewalls 124 and a dove tail channel 126. The channel 126 is defined by a first planar sidewall 128, opposing perpendicular sidewalls 130 and flange sidewalls 132 of flange 134. Here again, the sidewalls 132 are made to slidably receive the pectus bar 10 being shaped to have an arcuate contour. The pectus bar 10 may be secured to the stabilizer 112 by way of a rivet 90 passing through a hole (not shown) centered within the channel 126 or by way of the arcuate contour formed within the pectus bar 10. Alternatively, since the stabilizer 112 is primarily to prevent the pectus bar 10 from rotating 180° which is prevented by the flange 134, slight axial movement of the stabilizer 112 relative to the longitudinal axis of the pectus bar 10 may be tolerated. In this way, the stabilizer 112 can be secured relative to the pectus bar 10 by way of wrapping sutures about both the stabilizer 112 and the pectus bar 10 to provide sufficient securement of the stabilizer 112 along the longitudinal axis of the pectus bar 10.

Alternatively, the pectus bar 10 may be secured to the stabilizer 112 by way of a pair of bolts 136 passing through holes 122 adjacent the flange 134, as shown in FIG. 17. In this way, the screw shaft 140 may be captured by a notch or scallop 24 of the pectus bar 10. Here again, the rivet 90 or other coupling mechanism may also be used.

Turning to FIGS. 18–19, a stabilizer 144 according to the teachings of a sixth preferred embodiment of the present invention, is shown. The stabilizer 144 has an outer shape substantially similar to the stabilizer 112 and in this regard, like reference numerals will be used to identify like structures. The stabilizer 144 includes a pair of channels 146 adapted to receive a pair of pectus bars 10 which will be positioned substantially parallel with one another. Each channel 146 is defined by a planar sidewall 148 and a pair of perpendicular opposing sidewalls 150. Passing through each channel is a bore 152 defined by a sidewall 154 and passing through the center of the stabilizer 144 is a bore 156 defined by sidewall 158. The bores 152 are operable to be aligned with the bore 28 in the first end 12 or the second end 14 of the pectus bar 10. The rivet 90 or other appropriate coupling mechanism can then be used to secure the stabilizer 144 relative to the pectus bars 10. The bore 156 is again used to receive sutures to provide further securement. The distance between each channel 146 is generally determined by the distance between the patient's ribs.

Turning to FIGS. 20–21, a stabilizer 160 according to the teachings of a seventh preferred embodiment of the present invention, is shown. The stabilizer 160 is pivotably coupled to a pectus bar 162, via a nut and bolt 164 or other coupling mechanism passing through bores 166 and 168, respectively. The pectus bar 162 is substantially similar to the pectus bar 10, except that the end 170 of the pectus bar 162 includes a step 172 to define a clearance area 173 to retain a portion of the stabilizer 160. The stabilizer 160 has a shape which is substantially similar to the stabilizer 112 except that no channel or slot is provided. The stabilizer 160 is rotatably or pivotably secured to the pectus bar 162 such that upon insertion of the pectus bar 162 into the chest cavity, the stabilizer 160 is rotated about 90° clockwise or counter-clockwise to create a T-shaped end.

Finally, referring to FIGS. 22–23, a stabilizer 176 according to the teachings of an eighth preferred embodiment of the present invention, is shown. Here again, the stabilizer 176 is pivotably secured relative to a pectus bar 178. The pectus bar 178 is substantially similar to the pectus bar 10, except that each end 180 of the pectus bar 178 includes or defines a U-shaped slot 182 which is operable to retain a portion of the stabilizer 176. The stabilizer 176 is pivotably secured to the pectus bar 178, via a compression rivet 184 or other appropriate coupling element which passes through bore 186 of the pectus bar 178 and bore 188 within the stabilizer 176. Upon inserting the pectus bar 178 within the chest cavity, the stabilizer 176 can be rotated about 90° either clockwise or counter-clockwise to create a substantially T-shaped stabilizing mechanism.

Referring to FIGS. 24–32, the surgical instrumentation and procedure for performing pectus excavatum repair will now be discussed in further detail. Initially, a patient's chest 190, as shown in FIG. 26, is measured prior to surgery with the correctly sized pectus bar 10 selected based upon the patient's chest size and overall concave deformity, identified by reference numeral 192. The size and strength of the pectus bar 10 selected must be strong enough to support the chest 190 in the corrected position even when the patient sustains unexpected trauma. The pectus bar 10 remains within the patient for about a two-year period and thus needs to be long enough to accommodate for growth during this two-year period since the majority of the patients are small children.

Two pectus bars 10 are generally more effective than a single pectus bar 10, but in some situations may cause over-correction in some patients. Patients with Marfan's syndrome or other related tissue diseases generally have soft bone and, therefore, require two pectus bars 10 in order to distribute the pressure over a wider area. Generally, with a more severe deformity 192 or in older patients, a higher bendable strength and bendable stiffness pectus bar 10 is required versus a patient having a less severe deformity 192 or a younger patient since the sternum is more malleable with the younger patient. It has been found that at least a minimum bendable strength of about 65 in-lbs or a minimum bendable stiffness of about 1000 lb-in$^2$, as defined by ASTM F382-95 or with a material that has a yield strength of at least about $35 \times 10^6$ is required for generally all patients. Preferably, the material utilized for the pectus bar 10 is a cold-worked 316 LVM stainless steel which is capable of providing the minimal bendable strength, bendable stiffnesses or yield strength.

Once the properly sized and strength pectus bar 10 is selected, the selected pectus bar 10 is bent into an initial convex shape prior to surgery. At the time of surgery, a patient is positioned with both arms 194 abducted at the shoulder 196 to allow access to the lateral chest wall 190. The previously selected pectus bar 10 is then placed on the patients chest 190 and bent into its final desired shape to conform to the desired anterior chest wall curvature. The pectus bar 10 is custom bent into this desired shape by using a pectus bar bender 198, as shown in FIG. 24. The pectus bar bender 198 includes a pair of handles 200, which pivot about a contour wheel 202 under spring tension from spring 204. A pair of rollers 206 are used for shaping the pectus bar 10 against the contour wheel 202 upon drawing the handles 200 together. The pectus bar 10 is positioned substantially perpendicular to the bender 198 between the rollers 206 and the contour wheel 202. In this way, the surgeon can easily shape the pectus bar 10 to any desired curvature upon placing the pectus bar 10 between the rollers 206 and the contour wheel 202 and squeezing the handles 200, as shown in FIG. 24.

Once the pectus bar 10 is finally shaped to conform substantially to the anterior chest wall curvature with a slightly exaggerated curve to allow for anterior chest wall pressure, a transverse incision 208 of about 2.5 cm long is made on each side of the lateral chest wall 190 between the anterior axillary and posterior axillary lines, as shown in FIG. 26. A pectus bar umbilical tape puller 210, as shown in FIG. 25 is then used to shape a tunnel under and adjacent to the sternum and to draw an umbilical tape 212 through a tunnel 214 formed by the puller 210. The excavation of the tunnel may be facilitated by insertion of a thoracoscope into the chest to allow visualization of the tape puller as it comes through the mediastinum. The pectus bar umbilical tape puller 210 has a substantially cylindrical body 216 which forms a handle 218 at the proximal end and a curved blunt tip 220 at the distal end. As the body 216 extends to the curved distal tip 220, the diameter of the cylindrical body 216 tapers to a smaller diameter. At the curved distal tip 220 there is defined a umbilical tape hole 222 which is operable to receive the umbilical tape 212. It should further be noted that a conventional Kelly clamp may also be used in place of the umbilical tape puller 210 and used in substantially the same way as described herein.

Upon grasping the umbilical tape puller 210 with the handle 218, the skin tunnel 214 is raised anteriorly and the previously selected intercostal space is entered with the umbilical tape puller 210. The puller 210 is slowly advanced across the mediastinum immediately under the sternum until it is emerged on the opposite side, as shown in FIG. 26. The umbilical tape 212 is then passed through the hole 222 and through the tunnel 214. Once the strand of umbilical tape 212 is passed through the tunnel 214, the umbilical tape 212 may then be used to guide the puller 210 or the Kelly clamp from the opposite side to make sure that the tunnel 214 is wide enough to receive the pectus bar 10.

Figure 30:
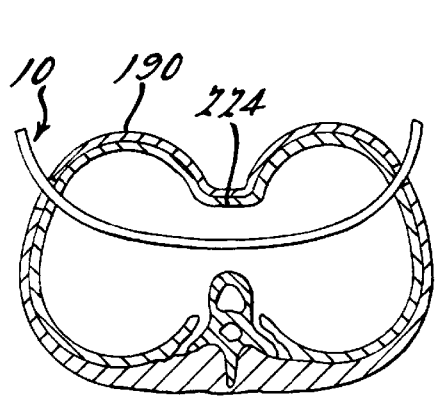
Figure 31:
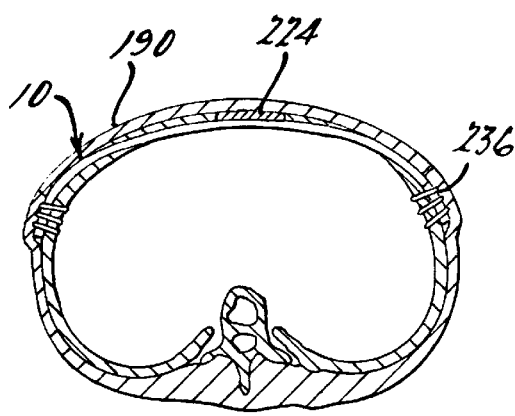

With the tunnel 214 properly prepared, the umbilical tape 212 is again routed through the tunnel 214 and the pectus bar 10 is secured to one end of the umbilical tape 212 through hole 28 in the pectus bar 10, as shown in FIG. 27. The pectus bar 10 is pulled beneath the sternum using the umbilical tape 212 for guiding and traction. The pectus bar 10 is passed under the sternum with the convexity facing posteriorly and the rounded ends 12 and 14 self-guiding the pectus bar 10, as shown in FIG. 30. With the pectus bar 10 in position, the pectus bar 10 is turned over about 180° so that the convexity faces anteriorly, thereby raising the sternum 224 and anterior chest wall 190 into the desired position, as shown in FIGS. 30 and 31.

The pectus bar 10 is turned or rotated using a pectus bar flipper 226, as shown in FIG. 28. The pectus bar flipper 226 includes a handle 228, a shaft 230 and an engagement head 232. The shaft 230 is appropriately bent such that when the engagement head 232 is engaged with the pectus bar 10, the flipper 226 is positioned substantially away from the chest cavity 190. The engagement head 232 defines a receiving slot 234 which is operable to slidably receive either the first end 12 or the second end 14 of the pectus bar 10. It should further be noted that in place of the flipper 226, a vice grip or other appropriate instrument may also be used to rotate the pectus bar 10.

Figure 32:
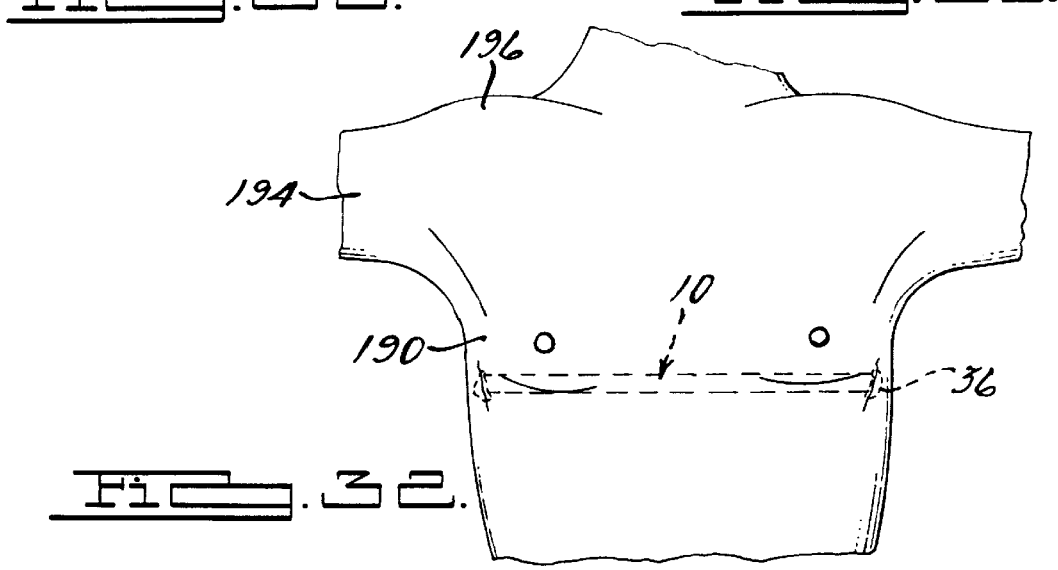

Once the first pectus bar 10 is set in the desired position, a second pectus bar 10 may be placed superiorly or inferiorly, if required. The pectus bar 10 may then be secured to the lateral chest wall muscles with heavy sutures 236. If the pectus bar is unstable, one of the above-identified stabilizers may be attached to one or both ends of the pectus bar 10. If two pectus bars 10 are used, the stabilizers which are operable to receive a pair of pectus bars 10 are connected to both ends to substantially form a rectangular cage. As shown in FIG. 32, using the stabilizers 36, the stabilizers 36 are slid onto the first end 12 and the second end 14 of the pectus bar 10. The stabilizers 36, as well as the pectus bar 10, are then secured with the heavy sutures 236 to the lateral chest wall muscles.

Once the stabilizers 36 and the pectus bar 10 are properly secured, positive end expiratory pressure (PEEP) of 4 to 6 cm, $H_2O$ is added to the anesthetic ventilator to prevent air trappings. The tunnel 214 and incision 208 are then closed in layers with a chest radiograph being obtained in the operating room to confirm the desired results and to check for full lung expansion. Regular activity is generally permitted after the patient is fully recovered, which is usually at the end of about a 30-day period. The pectus bar 10 along with the stabilizers 36 are retained within the patient for about two-years in order to train the shape of the sternum 224 into its desired contour. Should a resorbable material be used for the stabilizers or the pectus bar 10, the implants would be resorbed over time without the need for subsequent removal. If a resorbable material is not used, the pectus bar 10 along with the stabilizers are removed after about two years on an outpatient basis. The chest wall deformity 192 is thus substantially eliminated with the sternum 224 retaining substantially all of its new contoured shape.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. An apparatus for performing pectus excavatum repair on a non-resected deformed sternum of a patient, said apparatus comprising:

a plurality of sutures; and an elongated pectus bar having a first end and a second end and adapted to be convexly curved between said first end and said second end, said first end of said elongated pectus bar having a first arcuate sidewall and said second end of said elongated pectus bar having a second arcuate sidewall, said first end and said second end adapted to be secured to the patient with said plurality of sutures and said convexly curved portion adapted to be slidably located beneath the non-resected deformed sternum, said pectus bar having a minimum bendable strength of about 65 in-lbs, as defined by ASTM F382-95, at any location along said pectus bar, whereby said elongated pectus bar is adapted to retrain the non-resected deformed sternum into a desired shape.

2. The apparatus as defined in claim 1 further comprising at least a first stabilizer operable to engage one of either said first end and said second end of said elongated pectus bar, said first stabilizer adapted to be secured to the patient with said plurality of sutures.

3. The apparatus as defined in claim 2 wherein said stabilizer has a substantially triangular shape and includes a channel to slidably receive one of either said first end and said second end of said elongated pectus bar.

4. The apparatus as defined in claim 3 wherein said channel includes a groove having a pair of opposed flanges.

5. The apparatus as defined in claim 2 wherein said stabilizer is operable to slidably receive a first elongated pectus bar and a second elongated pectus bar.

6. The apparatus as defined in claim 2 wherein said stabilizer is pivotably secured to one of either said first end and said second end of said elongated pectus bar.

7. The apparatus as defined in claim 2 wherein said stabilizer defines at least a first hole and a plurality of notches, said hole and said plurality of notches operable to securably receive a suture.

8. The apparatus as defined in claim 2 wherein said stabilizer is formed from a resorbable material.

9. The apparatus as defined in claim 1 wherein said elongated pectus bar includes a pair of elongated opposing sidewalls which define a plurality of arcuate notches.

10. The apparatus as defined in claim 1 wherein said elongated pectus bar has a minimum yield strength of about $35 \times 10^6$ psi.

11. The apparatus as defined in claim 1 wherein said elongated pectus bar has a width between about 5 mm to about 20 mm.

12. The apparatus as defined in claim 1 wherein said elongated pectus bar has a minimum bendable stiffness of about 1000 lb-in$^2$, as defined by ASTM F382-95.

13. The apparatus as defined in claim 1 wherein said elongated pectus bar includes a plurality of bars providing an accumulated minimum bendable strength of about 65 in-lbs, as defined by ASTM F382-95.

14. The apparatus as defined in claim 13 wherein said plurality of bars is selected from the group consisting of cylindrical bars and rectangular bars.

15. The apparatus as defined in claim 1 wherein said elongated pectus bar is formed from a cold worked stainless steel.

16. An apparatus for performing pectus excavatum repair on a non-resected deformed sternum of a patient, said apparatus comprising:

a plurality of sutures; and an elongated pectus bar having a first end and a second end and adapted to be convexly curved between said first end and said second end, said first end of said elongated pectus bar having a first arcuate sidewall and said second end of said elongated pectus bar having a second arcuate sidewall, said first end and said second end adapted to be secured to the patient with said plurality of sutures and said convexly curved portion adapted to be slidably located beneath the non-resected deformed sternum, said elongated pectus bar having a minimum bendable stiffness of about 1000 lb-in$^2$, as defined by ASTM F382-95, at any location along said pectus bar, whereby said elongated pectus bar is adapted to retrain the deformed sternum into a desired shape.

17. The apparatus as defined in claim 16 wherein the elongated pectus bar has a minimum bendable strength of about 65 in-lbs, as defined by ASTM F382-95, at any location along said elongated pectus bar.

18. The apparatus as defined in claim 16 wherein said elongated pectus bar has a minimum yield strength of about 35×10$^6$ psi.

19. The apparatus as defined in claim 16 wherein said elongated pectus bar includes a plurality of bars providing a cumulative minimum bendable stiffness of about 1000 lb-in$^2$, as defined by ASTM F382-95.

20. The apparatus as defined in claim 16 further comprising at least a first stabilizer operable to engage one of either said first end and said second end of said elongated pectus bar, said first stabilizer adapted to be secured to the patient with said plurality of sutures.

21. The apparatus as defined in claim 16 further comprising an umbilical tape puller having a first end and a second end, said umbilical tape puller including a handle at said first end and a curved tip at said second end which is operable to receive umbilical tape, said umbilical tape puller operable to form a cavity adjacent the deformed sternum.

22. The apparatus as defined in claim 16 further comprising a bender operable to shape said elongated pectus bar into a convexly curved bar, said bender including a pair of handles which pivot about a contour wheel and a pair of rollers operable to engage said elongated pectus bar.

23. The apparatus as defined in claim 16 further comprising a flipper having a first end and a second end, said first end including a handle and said second end defining a bore operable to slidably receive one of either said first end and said second end of said elongated pectus bar.

24. An apparatus for performing pectus excavatum repair on a non-resected deformed sternum of a patient, said apparatus comprising:
a plurality of sutures; and
an elongated pectus bar having a first end and a second end and adapted to be convexly curved between said first end and said second end, said first end of said elongated pectus bar having a first arcuate sidewall and said second end of said elongated pectus bar having a second arcuate sidewall, said first end and said second end adapted to be secured to the patient with said plurality of sutures and said convexly curved portion adapted to be slidably located beneath the non-resected deformed sternum, said elongated pectus bar having a minimum yield strength of about 35×10$^6$ psi, whereby said elongated pectus bar is adapted to retrain a non-resected deformed sternum into a desired shape.

25. The apparatus as defined in claim 24 wherein said elongated pectus bar has a minimum bendable strength of about 65 in-lbs and a minimum bendable stiffness of about 1000 lbs-in$^2$.

26. A method for performing pectus excavatum repair on a non-resected deformed sternum, said method comprising:
providing an elongated pectus bar having a first end and a second end;
shaping the pectus bar into a convexly curved pectus bar;
passing the pectus bar under the non-resected deformed sternum with the convexity facing posteriorly; and
rotating the pectus bar so that the convexity faces anteriorly, whereby the non-resected deformed sternum is raised into a desired position.

27. The method as defined in claim 26 further comprising providing a pectus bar having a minimum bendable strength of about 65 in-lbs, as defined by ASTM F382-95.

28. The method as defined in claim 26 further comprising providing a pectus bar having a material with a minimum yield strength of about 35×10$^6$ psi.

29. The method as defined in claim 26 further comprising providing a pectus bar having a minimum bendable stiffness of about 1000 lb-in$^2$, as defined by ASTM F382-95.

30. The method as defined in claim 26 further comprising securing a stabilizer to one of either the first end or the second end of the elongated pectus bar.

31. The method as defined in claim 26 further comprising:
tying umbilical tape to an end of the elongated pectus bar; and
pulling the elongated pectus bar under the sternum upon pulling the umbilical tape through a pre-formed cavity.

32. The method as defined in claim 26 further comprising slidably engaging one of either the first end and the second end of the elongated pectus bar with a flipper defining a slot operable to slidably receive the pectus bar.

33. The method as defined in claim 26 wherein providing an elongated pectus bar further includes providing a plurality of bars.

* * * * *

UNITED STATES PATENT AND TRADEMARK OFFICE
CERTIFICATE OF CORRECTION

PATENT NO. : 6,024,759
DATED : February 15, 2000
INVENTOR(S) : Donald Nuss et al.

It is certified that error appears in the above-identified patent and that said Letters Patent is hereby corrected as shown below:

Column 4,
Line 5, delete "a" and substitute -- an -- therefor.

Column 8,
Line 24, delete "stabalizer 10" and substitute -- stabalizer 100 -- therefor.
Line 32, delete "sixth" and substitute -- fifth -- therefor.

Column 10,
Line 16, delete "patients" and substitute -- patient's -- therefor.
Line 48, delete "a" and substitute -- an -- therefor.

Signed and Sealed this

Thirty-first Day of December, 2002

JAMES E. ROGAN
*Director of the United States Patent and Trademark Office*